United States Patent
Berry

(10) Patent No.: US 7,384,431 B2
(45) Date of Patent: Jun. 10, 2008

(54) HEIGHT ADJUSTABLE VERTEBRAL BODY AND DISC SPACE REPLACEMENT DEVICES

(75) Inventor: Bret M. Berry, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 274 days.

(21) Appl. No.: 11/107,035

(22) Filed: Apr. 15, 2005

(65) Prior Publication Data

US 2005/0187634 A1  Aug. 25, 2005

Related U.S. Application Data

(63) Continuation of application No. 10/393,464, filed on Mar. 20, 2003, now abandoned.

(51) Int. Cl.
*A61F 2/44* (2006.01)
(52) U.S. Cl. .................................. 623/17.15
(58) Field of Classification Search ... 623/17.11–17.16
See application file for complete search history.

(56) References Cited

U.S. PATENT DOCUMENTS

| | | | |
|---|---|---|---|
| 4,401,112 A | 8/1983 | Rezaian |
| 4,553,273 A | 11/1985 | Wu |
| 4,554,914 A | 11/1985 | Kapp et al. |
| 4,657,550 A | 4/1987 | Daher |
| 4,820,305 A | 4/1989 | Harms et al. |
| 4,932,975 A | 6/1990 | Main et al. |
| 5,108,395 A | 4/1992 | Laurain |
| 5,192,327 A | 3/1993 | Brantigan |
| 5,236,460 A | 8/1993 | Barber |
| 5,458,641 A | 10/1995 | Ramirez Jimenez |
| 5,534,029 A | 7/1996 | Shima |
| 5,571,190 A | 11/1996 | Ulrich et al. |
| 5,571,192 A | 11/1996 | Schonhoffer |
| 5,674,296 A | 10/1997 | Bryan et al. |
| 5,702,451 A | 12/1997 | Biedermann et al. |
| 5,702,455 A | 12/1997 | Saggar |
| 5,766,253 A | 6/1998 | Brosnahan, III |
| 5,776,198 A | 7/1998 | Rabbe et al. |
| 5,876,457 A | 3/1999 | Picha et al. |
| 5,895,428 A | 4/1999 | Berry |
| 5,989,290 A | 11/1999 | Biedermann et al. |
| 6,015,436 A | 1/2000 | Schonhoffer |
| 6,086,613 A | 7/2000 | Camino et al. |
| 6,106,557 A | 8/2000 | Robioneck et al. |
| 6,159,211 A | 12/2000 | Boriani et al. |
| 6,193,756 B1 | 2/2001 | Studer et al. |
| 6,200,348 B1 | 3/2001 | Biedermann et al. |

(Continued)

FOREIGN PATENT DOCUMENTS

DE           202 13 013 U1       12/2002

(Continued)

*Primary Examiner*—Bruce Snow
(74) *Attorney, Agent, or Firm*—Krieg DeVault LLP

(57) ABSTRACT

A vertebral replacement device for supporting adjacent vertebrae includes a vertebral body or vertebral body member having at least one of an upper or lower member adjustably engaged at one end thereof. A spacer can be engaged to the upper or lower member to further increase the height of the vertebral replacement device. The vertebral replacement device can have a chamber extending therethrough for fusion of the supported vertebrae.

20 Claims, 4 Drawing Sheets

U.S. PATENT DOCUMENTS

| | | |
|---|---|---|
| 6,344,057 B1 | 2/2002 | Rabbe et al. |
| 6,660,038 B2 | 12/2003 | Boyer, II et al. |
| 6,758,862 B2 | 7/2004 | Berry et al. |
| 6,991,653 B2 | 1/2006 | White et al. |
| 2003/0045877 A1 | 3/2003 | Yeh |
| 2003/0181980 A1 | 9/2003 | Berry et al. |
| 2003/0191531 A1 | 10/2003 | Berry et al. |
| 2004/0236427 A1 | 11/2004 | Berry et al. |
| 2006/0116770 A1 | 6/2006 | White et al. |

FOREIGN PATENT DOCUMENTS

| | | |
|---|---|---|
| EP | 1 080 703 | 3/2001 |
| WO | WO 99/56675 | 11/1999 |
| WO | WO 03/079939 | 10/2003 |

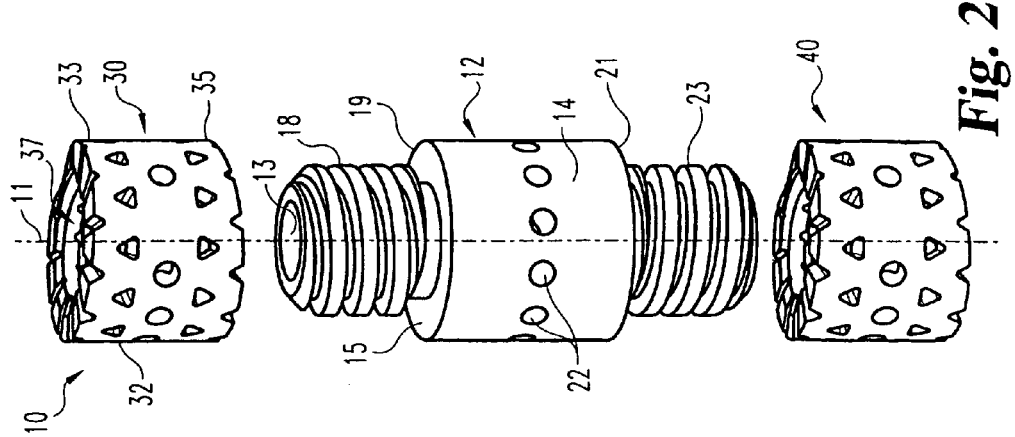
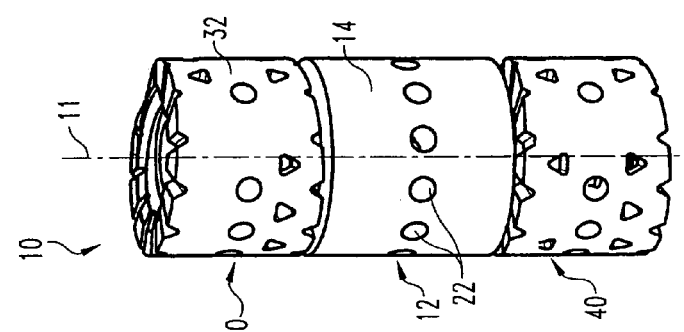
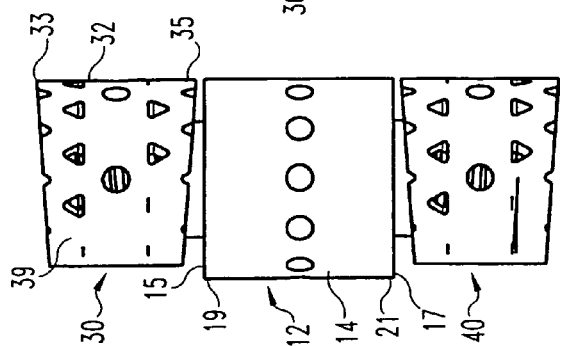
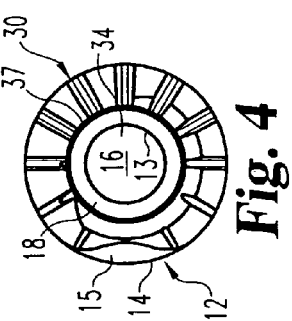
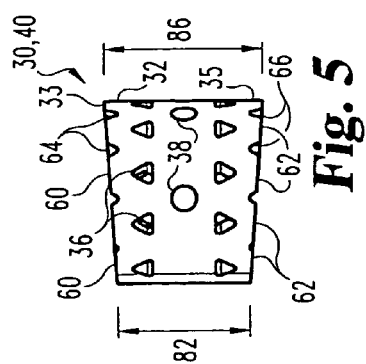
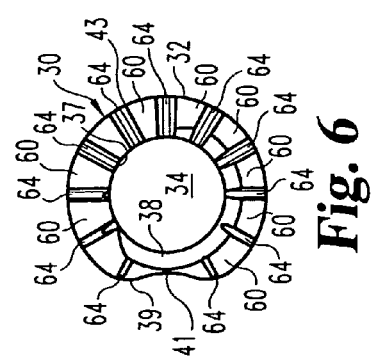

HEIGHT ADJUSTABLE VERTEBRAL BODY AND DISC SPACE REPLACEMENT DEVICES

This application claims priority to and is a continuation of U.S. patent application Ser. No 10/393,464 filed on Mar. 20, 2003, now abandoned.

BACKGROUND

The present invention is directed to devices for replacement of one or more vertebral bodies and/or one or more disc spaces between vertebrae of a spinal column.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong or stable as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material. Devices have also been provided to replace a removed vertebral body and to provide a support structure between the remaining vertebrae on either side of the one or more removed vertebral bodies.

There remains a need for improved devices for replacing one or more vertebral bodies and/or one or more disc spaces in a spinal column. The present invention is directed to satisfying these needs, among others.

DESCRIPTION OF THE FIGURES

FIG. 1 is a perspective view of a vertebral replacement device according to one embodiment of the present invention.

FIG. 2 is an exploded perspective view of the vertebral replacement device of FIG. 1.

FIG. 3 is a side elevation view of the vertebral replacement device of FIG. 1.

FIG. 4 is an end view of the vertebral replacement device of FIG. 1.

FIG. 5 is an elevational view of an end member comprising a portion of the vertebral replacement device of FIG. 1.

FIG. 6 is an end view of the end member of FIG. 5.

DESCRIPTION OF THE ILLUSTRATED EMBODIMENTS

Figures 7, 8:
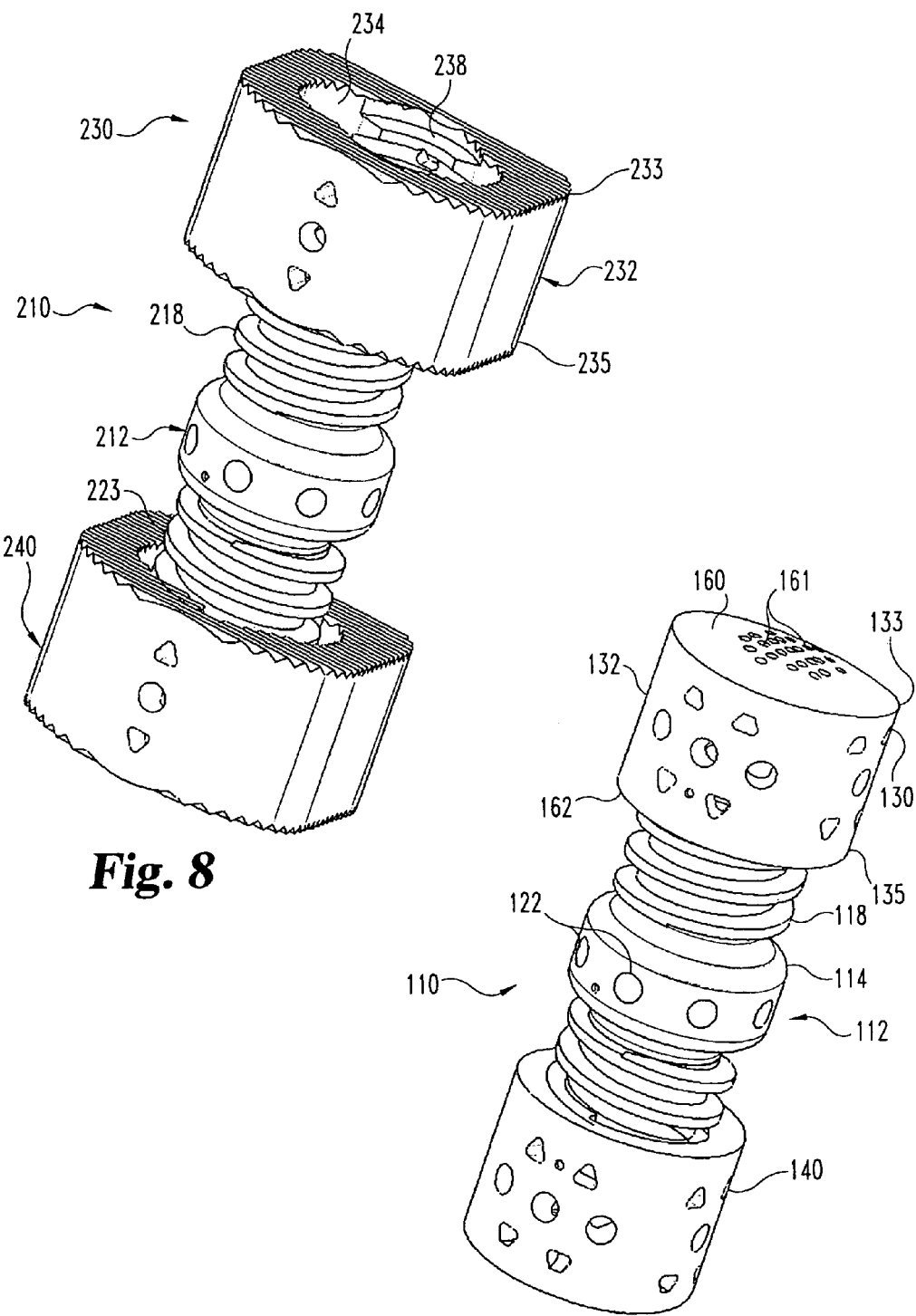
FIG. 7 is a perspective view of another embodiment vertebral replacement device.
FIG. 8 is a perspective view of another embodiment vertebral replacement device.

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The present invention relates to devices for replacing one or more vertebral bodies in the spinal column and/or one or more disc spaces between adjacent vertebrae. It is contemplated that the replacement devices will support adjacent ones of the intact vertebrae during fusion thereof. It is further contemplated that one or more components or members of the vertebral replacement devices can be positioned in a disc space between adjacent vertebrae for supporting the adjacent vertebrae during fusion. The vertebral replacement devices also have application in corpectomy and disc replacement procedures where fusion is not desired.

The vertebral replacement device can have a tubular form with a hollow chamber extending therethrough. Other forms are also contemplated, including devices without a hollow chamber, devices with multiple chambers, and devices with one or more chambers that extend only partially therethrough. The adjacent vertebrae are supported by opposite ends of the device and the chamber can be filled with bone growth inducing or osteogenetic material. The ends of the device include bearing surfaces to engage an adjacent vertebral endplates.

In one embodiment, the vertebral replacement device includes a connecting member and an upper member attached to an upper end of the connecting member and a lower member attached to a lower end of the connecting member. The upper and lower members can be adjusted relative to the connecting member to provide the desired overall height for the device. Each of the upper and lower members can have a generally kidney bean cross-sectional shape in the plane transverse to the central axis of the assembled device. Other cross-sectional shapes are also contemplated, including circular, racetrack-shaped, rectangular, square, oval, D-shaped, triangular, boomerang, banana, or other polygonal or non-circular shape. Each of the upper and lower members can include an interior chamber. The connecting member can also include an interior chamber that communicates with the interior chambers of the upper and lower members engaged thereto.

In one embodiment, the upper and lower members can be fabricated from a tubular mesh having apertures through its wall. One example of a tubular mesh is provided in U.S. Pat. No. 5,897,556, which is incorporated herein by reference in its entirety. Further forms contemplate that the upper and lower members and connecting member can be a tubular body with solid walls or wall structure including one or more openings.

The upper and lower members can be rotatably engaged with the connecting member. The connecting member includes an upper extension and a lower extension extending therefrom. The upper and lower extensions include a thread pattern to engage a thread pattern of the upper and lower members. The interlocking threads provide axial restraint of the upper and lower members relative to the connecting member, and allow the overall height of the device to be adjusted while maintaining axial restraint. In one embodiment, the extensions are received in an interior chamber or opening at respective ends of the upper and lower members.

In one embodiment, the upper and lower members include an interior chamber having a non-circular cross-section. The inner wall surface of the upper and lower members includes a thread pattern to threadingly engage upper and lower extensions of the connecting member. In one embodiment, the thread pattern is formed along only a portion of the inner wall surface extending around the non-circular chamber.

In one embodiment, the height of the device can be adjusted by adding one or more spacers to the end of at least one of the upper and lower members. The spacers can be axially secured to the respective upper or lower member by a flexible engaging member. In one form, an extension sleeve extends between chambers of the upper or lower member and the spacer to secure the spacer to the respective upper or lower member. In another form, one of the spacer and the adjacent upper or lower member includes an extension positionable in a chamber of the other of the spacer and the one of the upper or lower member.

Any one or all of the members of the vertebral replacement devices can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

Any suitable osteogenetic material or composition is contemplated for placement within chambers defined by the members of the vertebral replacement device. Such osteogenic material includes, for example, autograft, allograft, xenograft, demineralized bone, synthetic and natural bone graft substitutes, such as bioceramics and polymers, and osteoinductive factors. Where bony material is placed within the chambers of the components of the vertebral replacement device, the material can be pre-packed into the hollow chambers before the device is implanted, or can be pushed through the plurality of wall openings after the device is in position in the spinal column. A separate carrier to hold the materials within the chambers of the device can also be used. These carriers can include collagen-based carriers, bioceramic materials, such as BIOGLASS®, hydroxyapatite and calcium phosphate compositions. The carrier material can be provided in the form of a sponge, a block, folded sheet, putty, paste, graft material or other suitable form. Moreover, the osteogenetic compositions contained within the vertebral replacement device can comprise an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agent, held within a suitable carrier material.

In FIGS. 1-3, a vertebral replacement device 10 includes a connecting member 12, an upper member 30, and a lower member 40. Device 10 is illustrated as having a tubular form that extends along a longitudinal axis 11 and defines a chamber extending therethrough along axis 11. Bone growth can occur through this chamber for fusion between the vertebral bodies supported at each end of device 10. It is also contemplated that device 10 can be provided without a chamber extending therethrough. It is further contemplated that one or more of the members 12, 30, 40 is provided with a chamber, and that the other members are not.

Connecting member 12 includes a body 14 extending between an upper end 19 and an opposite lower end 21. Connecting member 12 further includes an upper extension 18 and a lower extension 23. Connecting member 12 includes an inner wall surface 13 (FIG. 5) that defines a chamber 16 extending between and opening at the outer ends of the extensions 18, 23. Each of the extensions 18, 23 extends outwardly from the respective end 19, 21 of body 14 and around chamber 16. End surface 15 extends around upper extension 18, and end surface 17 extends around lower extension 23. In the illustrated embodiment, extensions 18, 23 are threaded cylinders integrally formed with body 14 and extending from their respective end 19, 21. Other embodiments contemplate other forms for extensions 18, 23. For example, extensions 18, 23 can be in the form of externally threaded cylindrical sleeves that are separable from body 14 and engaged thereto by, for example, threadingly engaging internal threads along surface 13 of body 14. Other connections between body 14 and extensions 18, 23 are also contemplated, including friction fits, welded or fusion fits, end to end flanged fits with screws or bolts, bayonet locks, snap rings and the like.

The wall of body 14 includes a number of apertures 22 radially spaced about the mid-height thereof which extend through the wall and communicate with chamber 16. Various shapes for apertures 22 are contemplated, including circular and non-circular shapes such as a square, diamond, oval and/or rectangular shapes, and/or polygonal shapes. Apertures 22 can be engaged by an instrument to rotate body 14 in situ to adjust the overall height of device 10 while members 30, 40 are held in position by contact with the adjacent vertebral endplates or by external means. Members 30, 40 can also be rotated about the respective extensions 18, 23 to adjust the height of device 10. Various patterns for apertures 22 are also contemplated, including, for example, random patterns, axially spaced apertures, apertures positioned radially and axially about the entire body 14, and combinations thereof. A body 14 with no apertures is also contemplated.

Extensions 18, 23 can be provided with a substantially continuous thread extending along substantially the entire length of the corresponding extension 18, 23. Partially threaded extensions are also contemplated. The threads threadingly engage threads of the corresponding upper and lower members 30, 40 to resist axial dislocation of upper member 30 and lower member 40 away from and toward connecting member 12 along axis 11. To prevent rotation of upper and lower members 30, 40 when device 10 is positioned in the space between vertebrae, a set screw or other engagement member can be positioned through an aperture in the wall of the upper and lower members 30,40 and engage the respective extensions 18, 23. Rotation can additionally or alternatively be resisted by the axial compression forces on members 30, 40 by the adjacent vertebrae, the engagement of the outer ends of members 30, 40 with the adjacent vertebral endplates, and/or by providing locking engagement between the interfacing threads.

Referring also to FIGS. 5-6, upper and lower members 30, 40 are illustrated as being identical, although it is also contemplated that upper member 30 and lower member 40 can be provided with different configurations and/or sizes.

Only upper member 30 will be further described, it being understood that lower member 40 can be provided with identical features.

Upper member 30 includes a body 32 extending between an upper end 33 and a lower end 35. Body 32 has a height 82 between the upper and lower ends 33, 35. Height 82 can be selected so that upper member 30 fits within an intervertebral disc space between adjacent vertebrae. Upper end 33 and lower end 35 can be sloped to converge toward one another and form a height 86 opposite height 82. The sloped ends 33, 35 allow upper member 30 to restore and/or conform to the natural inclination between the adjacent endplates of the vertebral bodies. It is further contemplated that ends 33, 35 can be parallel to one another, or include a convex curvature. Still other embodiments contemplate that ends 33, 35 can include concave curvatures.

As shown in FIG. 6, body 32 has an inner wall surface 37 defining a chamber 34 that extends between and opens at ends 33, 35. A thread pattern 38 is provided along inner wall surface 37 to threadingly engage extension 18. Thread pattern 38 can extend along all or a portion of the height of body 32. Body 32 has an outer surface 39 that defines a kidney-shaped cross section transverse to longitudinal axis 11 that includes a concavely curved outer surface portion 41 and a convexly curved outer surface portion 43. Other cross-sectional shapes are also contemplated, including, for example, circular cross-sections and non-circular cross-sections, such as oval, triangular, square, rectangular, polygonal, boomerang shaped, D-shaped, or racetrack shaped cross-sections.

In the illustrated embodiment, body 14 of connecting member 12 has a circular cross-sectional shape transverse to longitudinal axis 11. Thus, as shown in FIG. 3, body 14 extends laterally beyond outer surface 39 of body 32 adjacent concavely curved portion 41. Body 14 can also be provided with the same shape as the upper and lower members 30, 40 to provide a vertebral replacement body device of uniform cross-sectional shape and size along its height.

Body 32 defines a number of triangular apertures 36 extending at least partially therethrough in communication with chamber 34, and a number of circular holes 38 extending at least partially therethrough from outer surface 39 of body 32. Holes 38 or the other holes can be threaded or otherwise sized and/or configured for engagement with one or more insertion instruments.

Body 32 further includes a number of bearing surfaces 60 spaced around first end 33 and bearing surfaces 62 spaced around second end 35. Adjacent ones of each of the bearing surfaces 60 are separated from one another by V-shaped recesses 64. Adjacent ones of each of the bearing surfaces 62 are separated from one another by V-shaped recesses 66. Bearing surfaces 60, 62 are planar and provide a number of plateau-like, generally flat bearing surfaces spaced about the respective end of body 32. Bearing surfaces 60, 62 have a trapezoidal shape as shown in FIG. 6, although other shapes are also contemplated. It is further contemplated that each end of body 32 could be provided with a single, continuous bearing surface extending around chamber 34, a continuous bearing surface enclosing or substantially enclosing chamber 34, and/or a bearing surface that bifurcates chamber 34.

The plateau-like bearing surfaces 60, 62 provide a surface area about the ends of body 32 for bearing support of the adjacent vertebral endplate and to resist subsidence of body 32 into the vertebrae. The plateau-like bearing surfaces 60, 62 provide surface area contact between the end of body 32 and the adjacent endplate, providing frictional resistance to body 32 sliding or twisting relative to the adjacent vertebral endplate. In the illustrated embodiment, bearing surfaces 60, 62 are formed by cutting body 32 through triangular apertures 36 that are radially spaced about body 32 and having their apices oriented away from the adjacent bearing surface. Since the triangular apertures are located at the same height about body 32, and ends 33, 35 are tapered, the depth and width of the recesses decrease toward the reduced height side of body 32, as shown in FIGS. 5 and 6.

Upper member 30 and lower member 40 are threadingly connected to respective ends of connecting member 12 to provide one embodiment vertebral replacement body device 10. Upper member 30 is threadingly advanced over upper extension 18 so that upper extension 18 extends into chamber 34. Lower member 40 is secured to lower extension 23 in a similar manner. It is contemplated that upper and lower members 30, 40 are positioned along the respective extensions 18, 23 so that upper and lower members are aligned with one another. For example, for upper and lower members 30, 40 provided with the kidney-shaped outer surface 39, concave surface portions 41 can be aligned along vertebral body member 10 to provide the desired fit in the disc space and so that the outer ends converge toward one another, as shown in FIG. 3.

Bearing surfaces 62 at lower end 35 of upper member 30 are spaced from end surface 15 extending about upper extension 18 of connecting member 12. The load from the spinal column is transmitted from upper member 30 to connecting member 12 through the threads engaging the members to one another. The space between the end surfaces of upper member 30 and body 12 provides additional locations for bone growth to stabilized device 10 in the space between vertebrae. The bearing surfaces of the lower member 40 are similarly spaced from end surface 17 extending about lower extension 23 of connecting member 12. As such, the end surfaces 15, 17 at the ends of body 14 and the adjacent bearing surfaces of the upper and lower members 30, 40 do not interdigitate or engage. Other embodiments contemplate that the ends of members 30, 40 can bear against the adjacent end surface 15, 17 of body 14 if the respective upper and lower members 30,40 are adjusted along the corresponding extension 18, 23 to provide such contact.

Device 10 can be used to replace a vertebra that has been removed from the spinal column segment using known techniques. Device 10 is assembled by securing upper member 30 to one end of connecting member 12 and securing lower member 40 to the other end of connecting member 12. This provides a vertebral replacement device 10 that has an overall height that is adjustable to provide the desired fit in the space between the vertebrae.

Vertebral replacement device 10 can be placed between a pair of intact vertebrae remaining after removal of vertebra 72. Replacement of more than one vertebra is also contemplated. A stabilization construct can be engaged to and extend between the intact vertebrae to support and stabilize the spinal column segment. The stabilization construct can be a rod system, plate system and/or artificial ligament system, for example. It is further contemplated that stabilization construct could be attached to any portion of the remaining vertebrae, including the anterior, antero-lateral, lateral, postero-lateral and/or posterior portions.

It is also contemplated that the upper and lower ends of upper and lower members 30, 40 could be provided with the same or differing angles of inclination. It is further contemplated that device 10 can comprise a kit having a number of upper members 30 and lower members 40 of various sizes, inclinations and/or heights 82, 84. A kit could also include a number of connecting members 12 of various sizes and lengths of extensions 18, 23. Such a kit would provide the surgeon flexibility in selecting the appropriately size and height for members of a device 10 based on conditions encountered in surgery. Providing extensions 18, 23 with opposing left and right hand threads allows connecting member 12 of device 10 can act as a turnbuckle to adjust the spacing between members 30, 40 in situ. It is also contemplated that extensions 18, 23 can be provided with threads turning in the same direction.

It is contemplated that upper or lower members 30, 40 can, when separated from connecting member 12, be positioned in a disc space between adjacent vertebrae. The heights 82, 84 between ends 33, 35 can thus be sized accordingly. Upper and lower members 30, 40 can be sized and/or shaped for insertion as a single member in a disc space that provides bilateral support of the adjacent vertebrae, or sized for insertion in combination with a second member in a disc space to provide bilateral support. Insertion of members 30, 40 into a disc space can be conducted via any one or combination of approaches, including anterior, posterior, posterior-lateral, anterior-oblique and lateral approaches. Members 30, 40 can be positioned into the disc space through a retractor sleeve in minimally invasive procedures, or through retracted skin and tissue in open surgical techniques.

It is also contemplated that connecting member 12 could be provided with one end configured to bear against a vertebral endplate, and that only one of the upper and lower members 30, 40 is engaged to the other end of connecting member 12. The assembled device could then be placed between adjacent vertebrae with an end of connecting member 12 and an end of the selected upper or lower member 30, 40 in contact with the adjacent vertebral endplates.

Referring now to FIG. 7, another embodiment vertebral replacement device 110 includes connecting member 112 and upper and lower members 130, 140 threadingly engaged to extensions 118, 123. Connecting member 112 is similar to connecting member 12, but includes a body 114 having a height 113 minimized between extensions 118, 123. It is also contemplated that connecting member 112 can be provided without body 114, but rather as a cylinder extending between and having the same diameter as extensions 18, 23 to accommodate apertures 122. The thread pattern can extend along the entire length of the connecting member, are along a portion of the length adjacent the opposite ends thereof.

Upper and lower members 130, 140 can be identical, and are described with reference to upper member 130. Upper member 130 includes a body 132 extending between upper and lower ends 133, 135. Bearing surface 160 at upper end 133 extends substantially across the entire width of body 132 and is convexly curved to conform to the vertebral endplate anatomy against which it is positioned. Bearing surface 160 includes a plurality of holes 161 to accommodate bone growth therethrough, although a solid bearing surface 160 is also contemplated. Holes 161 can communicate with a chamber extending into body 132, and also a chamber extending through connecting member 112.

Lower end 135 includes bearing surface 162 extending about a chamber opening at end 135. Bearing surface 162 is substantially continuous, although other surface patterns discussed herein are also contemplated. The chamber of body 132 receives extension 118, and can include threads extending therein from the inner surface of body 132 to threadingly engage extension 118. Upper and lower members 130, 140 can thus be adjustably engaged and axially restrained relative to connecting member 112 for use in corpectomy procedures. It is further contemplated that upper and lower members 130, 140 can be used without connecting member 112 in disc space replacement procedures.

Referring now to FIG. 8, there is shown vertebral replacement device 210. Vertebral replacement device 210 includes a connecting member 212, which is identical to connecting member 112. An upper member 230 and a lower member 240 are threadingly engaged to respective ones of the extensions 218, 223 of connecting member 212. Upper and lower members 230, 240 can be identical to one another, and will be described with reference to upper member 230.

Figure 9:
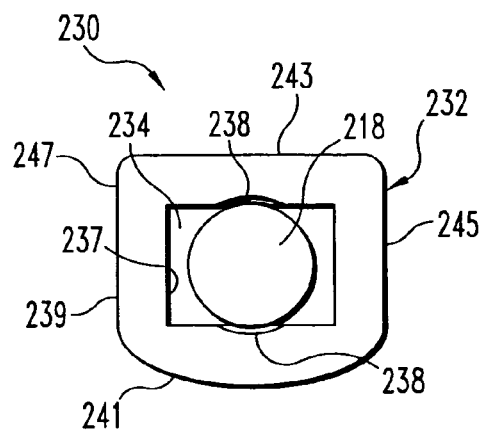
FIG. 9 is a plan view of the device of FIG. 8.

As further shown in FIG. 9, upper member 230 includes a body 232 having a chamber 234. Chamber 234 can extend completely or partially through the upper and lower ends 233, 235 of body 232. Chamber 234 opens toward lower end 235 to receive extension 218 therein. Body 232 includes an inner surface 237 defining chamber 234. Chamber 234 includes a non-circular shape transversely to the longitudinal axis of device 210, providing additional area for receipt and placement of bone growth material in chamber 234. Chamber 234 also provides open area about extension 218 in chamber 234, facilitating incorporation of connecting member 212 in the fusion of the adjacent vertebrae.

Inner wall surface 234 includes threaded portions 238 to threadingly engage extensions 218. Threaded portions 238 extend along only a portion of inner wall surface 237 that is contactable by extension 218, while the remainder of inner wall surface 237 can remain unthreaded.

Body 232 includes an outer surface 239 forming a D-shape having a convexly curved wall 241, an opposite linear wall 243, and parallel linear side walls 245, 247. Inner wall surface 237 defines a square shaped chamber 234. Other shapes for outer surface 239 and inner surface 237 are also contemplated, including circular and non-circular shapes, such as oval, square, kidney, boomerang, rectangular, polygonal, triangular, and various combinations of curved and linear wall segments.

Figure 10:
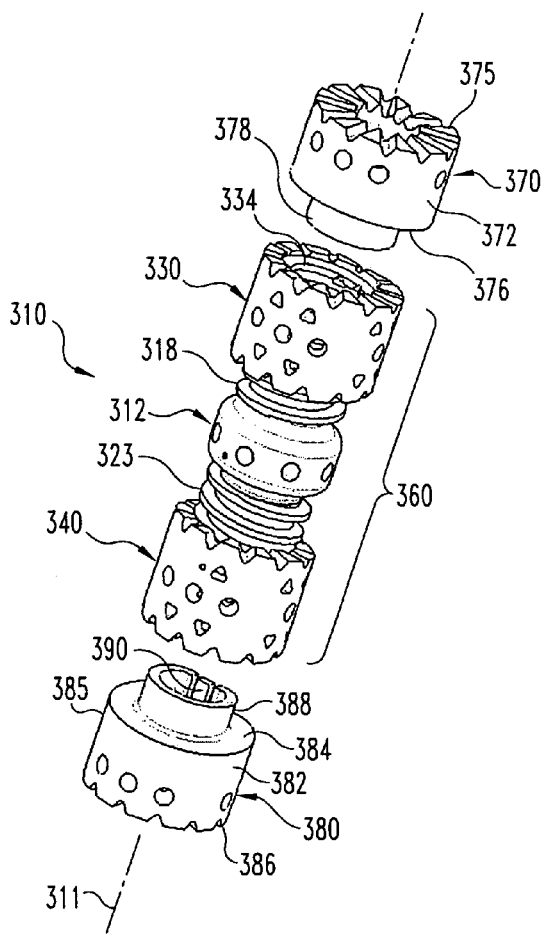
FIG. 10 is a partially exploded perspective view of another embodiment vertebral replacement device.

Referring to FIG. 10, another embodiment vertebral replacement device 310 is shown. Vertebral replacement device 310 includes a sub-assembly 360 that comprises a connecting member 312 and upper member 330 and a lower member 340. Connecting member 312, upper member 330 and lower member 340 can be similar to the embodiments discussed above, and provide a height adjustable sub-assembly 360 by threaded engagement of members 330, 340 with extensions 318, 323 of connecting member 312.

Vertebral replacement device 310 further includes an upper spacer 370 and a lower spacer 380. Spacer 370 includes a body 372 extending between an upper end 375 and a lower end 376. A lower extension 378 extends downwardly from lower end 376 towards upper member 330. Similarly, lower spacer 380 includes a body 382 extending between an upper end 385 and a lower end 386. An upper extension 388 extends upwardly from upper end 385 towards lower member 330.

Figure 11:
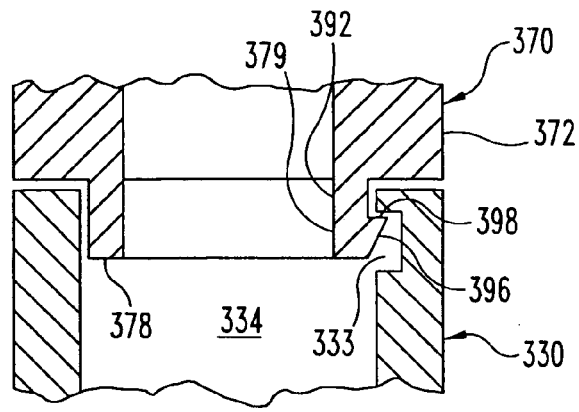
FIG. 11 is a section view showing the engagement between components of the vertebral replacement device of FIG. 10.
Figure 12:
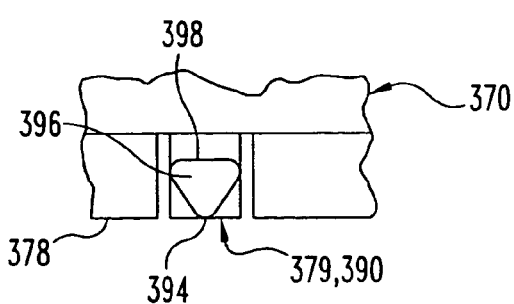
FIG. 12 is an elevation view of an engaging member comprising a portion of the vertebral replacement device of FIG. 10.

Referring further to FIGS. 11-12, each of the spacers 370, 380 include an engaging member in extensions 378, 388, respectively, such as shown with engaging member 390 of lower spacer 380. Extension 388 is positionable in the chamber (not shown) of lower member 340 and engages lower member 340 to axially secure lower spacer 380 thereto. The engaging member 379 of extension 378 similarly engages upper member 330 in chamber 334.

Engaging members 379, 390 secure upper spacer 370 and lower spacer 380 to respective ends of upper member 330 and lower member 340, resisting axial dislocation of spacers 370, 380 away from the respective upper and lower members 330, 340 along axis 311. Engaging members 379, 390 can also resist axial rotation of spacers 370, 380 relative to the respective upper and lower members 330, 340 about axis 311. Other embodiments contemplate that more than one engaging member 379, 390 can be provided in the wall of one or both of the extensions 378, 388.

Extensions 378, 388 are telescopingly received in upper and lower members 330, 340 until the adjacent ends bear against one another. Extensions 378, 388 can also resist lateral displacement of spacers 370, 380 relative to the engaged upper and lower member 330, 340 and also rotational displacement if provided with a non-circular interface therebetween.

As shown in FIGS. 11 and 12, engaging members 379, 390 include a projection or engaging portion 396 and a stem 392 connected or integrally formed with adjacent end of spacers 370, 380. Stem 392 has a reduced thickness to allow engaging members 379, 390 to deflect inwardly in response to a force applied to engaging portion 396. Engaging portion 396 projects outwardly from stem 392 and has a triangular shape tapering in thickness and width from an engaging surface 398 to an opposite outer end 394. In the illustrated embodiment, the triangular shaped engaging portion 396 fits within a triangular shaped recess 333 of the upper and lower members 330, 340. Recess 333 can open toward chamber 334, and can extend partially through the wall of member 330, or can extend completely through the wall and comprise a portion of an aperture thereof.

Other configurations for engaging members 379, 390 are also contemplated. For example, engaging members 379, 390 can be provided with an engaging portion 396 in the form of a partially spherical or rounded nub, a receptacle, rectangular or polygonal shaped tab or projection. Engaging portion 396 can have any size and shape that can be received in an aperture, recess and/or space opening in the inner wall surface of upper member 330 and lower member 340. In one embodiment, engaging portion 396 fits between adjacent thread turns on the inner wall surface of upper member 330 and lower member 340. Engaging members 379, 390 can also be in the form of a snap ring, collet, bayonet lock, or surface irregularity that resists axial movement of the spacer 370, 380 away from the engaged upper member 330 and lower member 340 along axis 311.

When secured to the respective upper and lower members 330, 340, spacers 370, 380 can bear against the adjacent end surfaces of the upper and lower member 330, 340 to provide axial restraint in compression. Engaging members 379, 390 provide axial restraint in tension away from the adjacent upper and lower member 330, 340. Torsional and lateral restraint of spacer members 370, 380 is provided by the interface between extensions 378, 388 and the inner wall of the respective coupling member 330, 340 to which spacer 370, 380 is engaged.

Spacer members 370 can be provided in a kit of a number of spacer members of various heights to provide further adjustment of the overall height of device 310. It is further contemplated that the spacer members can be used in isolation in a disc space as a disc replacement device for interbody fusion procedures, or positioned in side by-side relation with one another in a disc space for interbody fusion procedures. Spacers 370, 380 can be provided in any size, shape, height and end surface configuration as discussed above for the upper and lower members discussed herein.

In another embodiment, it is contemplated that upper and lower members 330, 340 are provided with an extension positionable in the chamber of the adjacent upper and lower spacer 370, 380. The extensions of the upper and lower members 330, 340 can include a flexible engaging member to engage an aperture, recess or other space in the respective upper and lower spacers 370, 380 in the manner discussed above with respect to extensions 378, 388 and engaging members 379, 390.

Figure 13:
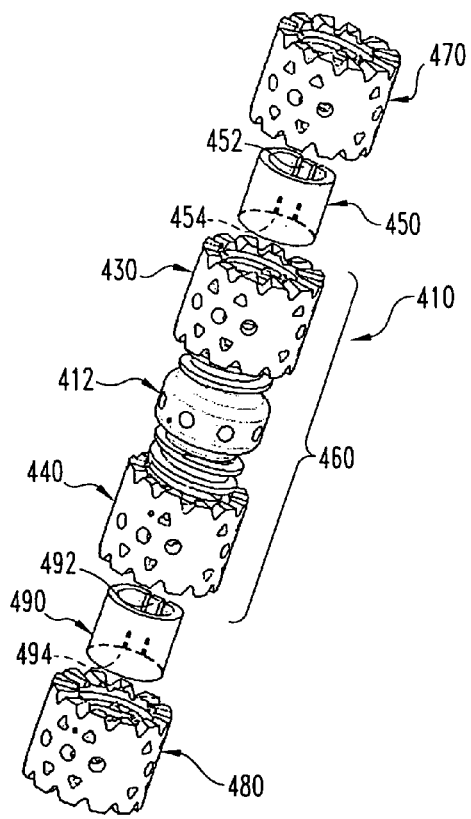
FIG. 13 is a partially exploded perspective view of another embodiment vertebral replacement device.

In FIG. 13 there is provided an alternate embodiment vertebral replacement device 410. Vertebral replacement device 410 includes a height-adjustable sub-assembly 460 including first disc replacement or upper member 430 and second disc replacement or lower member 440 adjustably engaged at opposite ends of a vertebral body or connecting member 412. Upper spacer 470 is engageable to upper member 430, and lower spacer 480 is engageable to lower member.

A first coupling member 450 includes a flexible engaging member 452 at one end thereof and a second flexible engaging member 454 at a second end thereof. Engaging members 452, 454 can be similar to engaging members 379, 390 discussed above. In the illustrated embodiment, engaging members 452, 454 are integrally formed in a wall of coupling member 450 an are resiliently deflectable inwardly as spacer 470 and upper member 430 are positioned thereover. Engaging members 452, 454 engage a recess or other structure in the corresponding spacer 470 and upper member 430 to axially constrain spacer member 470 to upper member 430. A second coupling member 490 is provided with engaging members 492, 494 to similarly secure spacer 480 to lower member 440.

Coupling members 450, 490 are illustrated in the form of cylindrical sleeves with a central passage to allow bone growth therethrough. Coupling members 450, 490 can be provided with non-circular cross-sections to resist rotation of members 430, 440 and spacers 470, 480 relative thereto. It is further contemplated that coupling members 450, 490 can be provided with a solid body, or a body including a number of passages extending therethrough. In another form, coupling members 450, 490 are comprised of material facilitating bone growth. Coupling members 450, 490 can include one or more projections formed on an outer wall surface thereof to engage recesses in the inner wall surfaces of members 330, 340 and spacers 370, 380.

While the invention has been illustrated and described in detail in the drawings and foregoing description, the same is to be considered as illustrative and not restrictive in character. All changes and modifications that come within the spirit of the invention are desired to be protected.

What is claimed is:

1. A vertebral replacement device, comprising:
 a connecting member including a body and first and second threaded extensions extending from said body along a longitudinal axis;
 a first member threadingly engageable to said first threaded extension, wherein said first member includes a body extending between a first end and a second end, said body including a height between said first and second ends and adapted to restore a spinal disc space when said first member is positioned therein; and
 a second member threadingly engageable to said second threaded extension, wherein said second member includes a body extending between a first end and a second end, said body having a height between said first and second ends and adapted to restore a spinal disc space when said second member is positioned therein,
 wherein at least one of said first and second members includes first and second ends that are each sloped relative to a longitudinal axis of the vertebral replacement device, and wherein at least one of said first and second members includes an outer surface defining a kidney-shaped cross-section extending between said first and second ends thereof.

2. The device of claim 1 wherein said kidney-shaped cross-section is defined by a concavely curved outer surface portion adjoining an opposite convexly curved outer surface portion.

3. The device of claim 2, wherein said connecting member includes an outer surface defining a circular cross-section.

4. A vertebral replacement device, comprising:
a connecting member including a body and a first threaded extension extending from said body along a longitudinal axis; and
a first member threadingly engageable to said first threaded extension, wherein said first member includes a body extending between a first end and a second end, said body including a height between said first and second ends and adapted to restore a spinal disc space when said first member is positioned therein, wherein said first and second ends are sloped toward one another and are each sloped relative to said longitudinal axis, wherein said first member includes an outer surface defining a kidney-shaped cross-section extending from said first sloped end to said second sloped end of said body of said first member.

5. The device of claim 4, wherein said kidney-shaped cross-section is defined by a concavely curved outer surface portion adjoining an opposite convexly curved outer surface portion.

6. The device of claim 5, wherein said connecting member includes an outer surface defining a circular cross-section.

7. A vertebral replacement device, comprising:
a connecting member including a body and first and second threaded extensions extending from said body along a longitudinal axis, said body including an outer surface defining a circular cross-section; and
a first member threadingly engageable to said first threaded extension, wherein said first member includes a body extending between a first end and a second end, said body including a height between said first and second ends and adapted to restore a spinal disc space when said first member is positioned therein, wherein said first and second ends are each sloped relative to said longitudinal axis and said body includes an outer surface defining a kidney shaped cross-section extending from said first sloped end to said second sloped end.

8. The device of claim 7, wherein said first and second ends of said body of said first member are sloped toward one another.

9. The device of claim 8, wherein said first member defines a hollow chamber extending between said first and second ends for receiving said first threaded extension therein.

10. The device of claim 7, wherein said kidney-shaped cross-section is defined by a concavely curved outer surface portion adjoining an opposite convexly curved outer surface portion.

11. The device of claim 7, wherein said second threaded extension extends along said longitudinal axis opposite said first threaded extension, and further comprising a second member threadingly engageable to said second threaded extension, wherein said second member includes a body extending between a first end and a second end, said body having a height between said first and second ends and adapted to restore a spinal disc space when said second member is positioned therein.

12. The device of claim 11, wherein said body of said second member includes an outer surface defining a kidney-shaped cross-section between said first and second ends.

13. The device of claim 7, wherein said body of said connecting member includes first and second end surfaces extending around respective ones of said first and second extensions, and said first and second extensions extend outwardly from said body from said respective first and second end surfaces.

14. The device of claim 13, wherein one of said first and second ends of said first member is spaced from said first end surface of said body of said connecting member to provide a location for bone growth between said first member and said connecting member when said first member is threadingly engaged to said first threaded extension.

15. The device of claim 13, wherein one of said first and second ends of said first member contacts said first end surface of said body of said connecting member to bear said first member against said connecting member when said first member is threadingly engaged to said first threaded extension.

16. The device of claim 4, wherein said body of said connecting member includes a first end surface said first extension, and said first extension extends outwardly from said body from said respective first end surface.

17. The device of claim 16, wherein one of said first and second ends of said first member is spaced from said first end surface of said body of said connecting member to provide a location for bone growth between said first member and said connecting member when said first member is threadingly engaged to said first threaded extension.

18. The device of claim 16, wherein one of said first and second ends of said first member contacts said first end surface of said body of said connecting member to bear said first member against said connecting member when said first member is threadingly engaged to said first threaded extension.

19. The device of claim 1, wherein:
said body of said connecting member includes first and second end surfaces extending around respective ones of said first and second extensions, and said first and second extensions extend outwardly from said body from said respective first and second end surfaces;
one of said first and second ends of said first member is spaced from said first end surface of said body of said connecting member to provide a location for bone growth between said first member and said connecting member when said first member is threadingly engaged to said first threaded extension; and
one of said first and second ends of said second member is spaced from said second end surface of said body of said connecting member to provide a location for bone growth between said second member and said connecting member when said second member is threadingly engaged to said second threaded extension.

20. The device of claim 1, wherein:
said body of said connecting member includes first and second end surfaces extending around respective ones of said first and second extensions, and said first and second extensions extend outwardly from said body from said respective first and second end surfaces;
one of said first and second ends of said first member contacts said first end surface of said body of said connecting member to bear said first member against said connecting member when said first member is threadingly engaged to said first threaded extension; and
one of said first and second ends of said second member contacts said second end surface of said body of said connecting member to bear said second member against said connecting member when said second member is threadingly engaged to said second threaded extension.

* * * * *